US007994140B2

(12) United States Patent
Meutermans et al.

(10) Patent No.: US 7,994,140 B2
(45) Date of Patent: Aug. 9, 2011

(54) CLASSES OF COMPOUNDS THAT INTERACT WITH GPCRS

(75) Inventors: Wim Meutermans, Queensland (AU);
Glang Le Thanh, Queensland (AU);
Giovanni Abbenante, Queensland (AU);
Gerald Tometzki, Queensland (AU);
Judy Halliday, Queensland (AU);
Johannes Zuegg, Queensland (AU)

(73) Assignee: Alchemia Limited, Queensland (AU)

( * ) Notice: Subject to any disclaimer, the term of this patent is extended or adjusted under 35 U.S.C. 154(b) by 922 days.

(21) Appl. No.: 10/530,851

(22) PCT Filed: Oct. 10, 2003

(86) PCT No.: PCT/AU03/01347
§ 371 (c)(1),
(2), (4) Date: Apr. 7, 2006

(87) PCT Pub. No.: WO2004/032940
PCT Pub. Date: Apr. 22, 2004

(65) Prior Publication Data
US 2006/0223764 A1 Oct. 5, 2006

(30) Foreign Application Priority Data
Oct. 11, 2002 (AU) .................. 2002951995

(51) Int. Cl.
*A61K 31/70* (2006.01)
*A01N 43/04* (2006.01)
*C07H 5/04* (2006.01)
*C07H 5/06* (2006.01)
*C07G 3/00* (2006.01)
*C08B 37/00* (2006.01)

(52) U.S. Cl. ............. 514/25; 514/42; 536/4.1; 536/18.7
(58) Field of Classification Search ........................ None
See application file for complete search history.

(56) References Cited

U.S. PATENT DOCUMENTS

| 4,376,207 A | 3/1983 | Uskokovic et al. |
| 4,495,346 A | 1/1985 | Anderson et al. |
| 4,548,923 A | 10/1985 | Hartmann et al. |
| 5,552,534 A * | 9/1996 | Hirschmann et al. ......... 536/17.4 |
| 5,811,512 A * | 9/1998 | Hirschmann et al. ......... 530/311 |
| 6,017,926 A | 1/2000 | Askew et al. |
| 6,030,942 A | 2/2000 | Cooperman et al. |
| 6,184,366 B1 | 2/2001 | Christ et al. |
| 6,417,172 B1 | 7/2002 | Rossignol et al. |
| 6,756,489 B1 | 6/2004 | Schmidt et al. |
| 7,138,531 B2 | 11/2006 | Sas et al. |
| 7,232,900 B2 | 6/2007 | Johnson et al. |
| 7,417,129 B2 | 8/2008 | West et al. |
| 2003/0232766 A1 | 12/2003 | West et al. |
| 2008/0176936 A1 | 7/2008 | Meutermans et al. |

FOREIGN PATENT DOCUMENTS

| DE | 102 59 844 | 7/2004 |
| WO | WO 93/17032 | 9/1993 |
| WO | WO 95/11686 | 5/1995 |
| WO | WO 97/28172 | 8/1997 |
| WO | 99/00406 | 1/1999 |
| WO | WO 99/07718 | 2/1999 |
| WO | WO 00/42057 | 7/2000 |
| WO | WO 01/36433 | 5/2001 |
| WO | 01/98270 A2 | 12/2001 |
| WO | WO 02/32915 | 4/2002 |
| WO | WO 02/085867 | 10/2002 |
| WO | WO 03/082846 | 10/2003 |
| WO | WO 2004/014929 | 2/2004 |
| WO | WO 2004/032940 | 4/2004 |

OTHER PUBLICATIONS (R) Kroeze et al., "G-Protein-Coupled Receptors [GPCRs] at a Glance," Journal of Cell Science, 116, 4867-4869 (2003).*
S. Budavari et al., "The Merck Index", Thirteenth Edition, pp. 793-794, monograph 4471, 2001.
Knapp et al, "Amino Alcohol and Amino Sugar Synthesis by Benzoylcarbamate Cyclization", J. Org. Chem. 55:5700-5710 (1990).
Ichikawa et al, "A new synthetic method for the preparation of amino sugars through an ally cyanate-to-isocyanate rearrangement", J. Chem. Soc. Perkin Trans. 1:1449-1455 (1997).
Bosserhoff, Anja-Katrin, "Integrins as targets in therapy", Expert Opin. Ther. Patents 16)7):963-975 (2006).
Arnaout et al, "Coming to grips with integrin binding to ligands: Opinion", Current Opinion in Cell Biology 14:641-651 (2002).
Boer et al, "Design, Synthesis, and Biological Evaluation of $\alpha_4\beta_1$ Integrin Antagonists Based on β-D-Mannose as Rigid Scaffold", Angew. Chem. Int. Ed. 40(20):3870-3873 (2001).
Clark and Brugge, "Integrins and Signal Transduction Pathways: The Road Taken", Science 268:233-238 (1995).
Hirschmann et al, "Modulation of Receptor and Receptor Subtype Affinities Using Diastereomeric and Enantiomeric Monosaccharide Scaffolds as a Means to Structural and Biological Diversity. A New Route to Ether Synthesis", Journal of Medicinal Chemistry 41(9):1382-1391 (1998).
Lehmann et al, "Role of αvβ5 and αvβ6 Integrin Glycosylation in the Adhesion of a Colonic Adenocarcinoma Cell Line (HT29-D4)", Journal of Cellular Biochemistry 61:266-277 (1996).

(Continued)

Primary Examiner — Lawrence E Crane
(74) Attorney, Agent, or Firm — Nixon & Vanderhye

(57) ABSTRACT

The present invention relates to a method of identifying a candidate therapeutic agent. The method comprises contacting a G-Protein Coupled Receptor (GPCR) with a compound of General Formula (I), or a pharmaceutically acceptable salt thereof

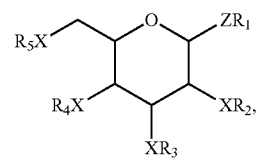

determining whether the compound inhibits or effects signal transduction activity of the GPCR, wherein a compound that inhibits or effects the activity of the GPCR is a candidate therapeutic agent.

19 Claims, No Drawings

OTHER PUBLICATIONS

Longhi et al, "Involvement of Membrane Carbohydrates of HeLa Cells in the *E. Coli* HB101 (pRI203) Invasive Pathway", Microbiologica 15:107-116 (1992).

Moitessier et al, "Design, Synthesis and Preliminary Biological Evaluation of a Focused Combinatorial Library of Stereodiverse Carbohydrate-Scaffold-Based Peptidomimetics", Bioorganic & Medicinal Chemistry 9:511-523 (2001).

Nicolaou et al, "Design, Synthesis and Biological Evaluation of Carbohydrate-Based Mimetics", Tetrahedron 53(26):8751-8778 (1997).

Stern et al, "Human Monocyte-Derived Macrophage Phagocytosis of Senescent Eosinophils Undergoing Apoptosis", American Journal of Pathology 149(3):911-921 (1996).

Du et al, "The recognition of three different epitopes for the H-type 2 human blood group determinant by lectins of Ulex europaeus, Galactia tenuiflora and Psophocarpus tetragonolobus (Winged Bean", Glycoconjugate Journal 11:443-461 (1994).

Advisory Action dated Feb. 10, 2011 issued in connection with U.S. Appl. No. 10/524,048.

Office Action dated Nov. 2, 2010 issued in connection with U.S. Appl. No. 10/524,048.

Hirschmann et al, "Nonpeptidal Peptidomimetrics with a β-D-Glucose Scaffolding. A Partial Somatostatin Agonist Bearing a Close Structural Relationship to a Potent, Selective Substance P Antagonist", J. Am. Chem. Soc. 114:9217-9218 (1992).

Gruner et al, "Carbohydrate-Based Mimetics in Drug Design: Sugar Amino Acids and Carbohydrate Scaffolds", Chem. Rev. 102:491-514 (2002).

Le et al, "Molecular diversity through sugar scaffolds", DDT 8(15):701-709 (2003).

Ye and Wong, "Anomeric Reactivity-Based One-Pot Oligosaccharide Synthesis: A Rapid Route to Oligosaccharide Libraries", J. Org. Chem. 65:2410-2431 (2000).

Christ, W. J., "New monosaccharide derivatives, useful as intermediates for substituted liposaccharides for treating endotoxemia such as sepsis, septicemia and toxic shock", Derwent Abstract Accession No. 2002-371191/40, Mar. 7, 2002.

Maletic et al, "Preparation of Potential Inhibitors of the Mur-Pathway Enzymes on Solid Support Using an Acetal Linker", Bioorganic & Medicinal Chemistry Letters 13:1125-1128 (2003).

Fukase et al, "New Efficient Route for Synthesis of Lipid A by using Affinity Separation", Synlett 11:1693-1698 (2001).

Nakayama et al, "Novel peptidomimetics of the antifungal cyclic peptide Rhodopeptin: design of mimetics utilizing scaffolding methodology", Organic Letters 3(22):3447-3450 (2001).

Yoshizaki et al, "First total synthesis of the Re-type lipopolysaccharide", Angew. Chem., Int. Ed. 40(8):1475-1480 (2001).

Hanessian et al, "Formation of p-alkoxybenzylidene acetals on solid support and generation of functional diversity with carbohydrate scaffolds", Synlett 1:102-104 (1999).

Carey and Sundberg, "Advanced Organic Chemistry, Part B: Reactions and Synthesis", Copyright 2001, Kulwer Academic/Plenum Publishers, pp. 831-835.

Greene et al, "Protective Groups in Organic Synthesis", published 1999 by John Wiley and Sons, Inc, pp. 494-653.

International Search Report dated Sep. 9, 2003 issued in connection with PCT/AU03/01008.

* cited by examiner

CLASSES OF COMPOUNDS THAT INTERACT WITH GPCRS

This application is the US national phase of international application PCT/AU2003/001347 filed 10 Oct. 2003 which designated the U.S. and claims priority of AU 2002951995, filed 11 Oct. 2002, the entire contents of each of which are hereby incorporated by reference.

FIELD OF THE INVENTION

The invention provides classes of biologically active compounds that interact in a pharmaceutically significant manner with G-Protein Coupled Receptors (GPCRs), pharmaceutical compositions containing such compounds and methods of treatment of humans suffering from a disorder which can be at least partially overcome by the compounds or compositions.

BACKGROUND OF THE INVENTION

The drug discovery landscape has been transformed by the genomics revolution. Advances in the understanding of biomolecular pathways and the roles they play in disease will lead to vast numbers of targets for therapeutic intervention. GPCRs represent the most important collection of therapeutic targets available.

GPCRs are proteins that tranduce signals across a cell membrane. They consist of a single polypeptide chain that threads back and forth seven times across the phospholipid bilayer that forms the cell membrane. The polypeptide chain has a portion inside the cell which form a G-protein coupling domain, and a receptor portion outside or in the cell wall. A signal molecule interacts with the receptor which sends the signal through the membrane wall and the signal causes the G-protein coupling domain to interact with a G protein.

Over 50% of marketed drugs target GPCRs. Whilst the druggable extent of GPCRS numbers some 450 receptors only some 200 GPCRS have been matched with their ligands. Orphan receptors suitable for drug targeting may therefore number in excess of 200 receptors. These are receptors with less than approximately 45% sequence identity to known GPCRs for which ligands have not been identified.

The targets of current GPCR drugs include, pain and inflammation, cancer, metabolic and gastrointestinal, cardiovascular and central nervous system disorders.

There is a continuing demand for new therapeutics, especially as our understanding of biological processes expands from the genomics revolution. The aforementioned GPCRs are suitable targets for therapeutic intervention due to their roles in such disorders as cancers, obesity and erectile dysfunction.

Considering the rate of generation and nature of the targets currently being deconvoluted by biologists, there is a need for the development of drug candidates, designed in a rational manner to purposely interact with selected targets, such as the GPCRs.

From a drug discovery perspective, carbohydrate pyranose and furanose rings and their derivatives are well suited as templates. Each sugar represents a three-dimensional scaffold to which a variety of substituents can be attached, usually via a scaffold hydroxyl group, although occasionally a scaffold carboxyl or amino group may be present for substitution. By varying the substituents, their relative position on the sugar scaffold, and the type of sugar to which the substituents are coupled, numerous highly diverse structures are obtainable.

An important feature to note with carbohydrates, is that molecular diversity is achieved not only in the type of substituents, but also in the three dimensional presentation. The different stereoisomers of carbohydrates that occur naturally, offer the inherent structural advantage of providing alternative presentation of substituents.

Employing a related methodology, Hirschmann et al (Hirschmann, R., et. al., J. Am. Chem. Soc., 1992, 114, 9217-9218, U.S. Pat. No. 5,552,534, WO 97/28172, WO 95/11686) synthesised several compounds designed as somatostatin analogues and integrin binders. The methodology employed by Hirschmann relied on protracted, linear, non-combinatorial syntheses, employed exclusively non-aminated pyranoses, and did not exploit any epimerisation chemistry to allow greater access to structural diversity. Consequently, these compounds and methods are manifestly distinct from this present invention.

We have developed a system that allows the chemical synthesis of highly structurally and functionally diverse derivatised carbohydrate and tetrahydropyran structures, of both natural and unnatural origin. The diversity accessible is particularly augmented by the juxtaposition of both structural and functional aspects of the molecules.

Using the axioms of this drug discovery methodology, we synthesised several novel classes of chemotypes in an effort to develop drug candidates against GPCR targets.

SUMMARY OF THE INVENTION

It is a general object of the invention to provide compounds that interact with GPCRs in a biologically significant manner, It is an optional object of the invention to provide a pharmaceutical formulation comprising at least one compound as described herein or a pharmaceutically acceptable salt thereof, together with one or more pharmaceutically acceptable carriers, diluents or excipients.

In one aspect the invention provides for compounds of general formula I, that interact with GPCRs in a biologically significant manner,

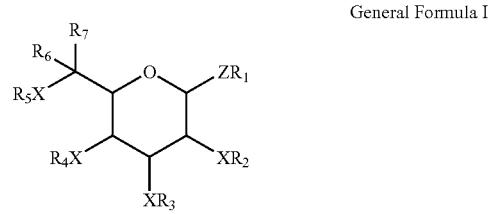

General Formula I

Wherein the ring may be of any configuration;

Z is sulphur, oxygen, $CH_2$, $C(O)$, $C(O)HNR^A$, NH, $NR^A$ or hydrogen, in the case where Z is hydrogen then $R_1$ is not present, $R^A$ is selected from the set defined for $R_1$ to $R_5$, X is oxygen or nitrogen providing that at least one X of General Formula I is nitrogen, X may also combine independently with one of $R_1$ to $R_5$ to form an azide, $R_1$ to $R_5$ are independently selected from the following definition which includes but is not limited to H or an alkyl, acyl, alkenyl, alkynyl, heteroalkyl, aryl, heteroaryl, arylalkyl or heteroarylalkyl substituent of 1 to 20 atoms, which is optionally substituted, and can be branched or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoaryl, aminoheteroaryl, thioalkyl, thioaryl or thioheteroaryl, which may optionally be further substituted, and $R_6$ and $R_7$ are hydrogen, or may combine to form a carbonyl function.

In one embodiment the invention provides for compounds of general formula II that interact with GPCRs in a biologically significant manner,

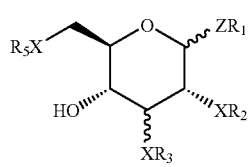

General Formula II

Wherein $R_1$, $R_2$, $R_3$, $R_5$, Z and X are defined as in General Formula I.

In a second embodiment the invention provides for compounds of general formula III that interact with GPCRs in a biologically significant manner,

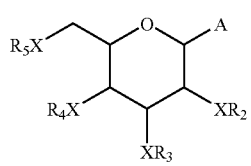

General Formula III

Wherein A is defined as hydrogen, $SR_1$, or $OR_1$ where $R_1$ is defined as in General Formula I, and
X and $R_2$ to $R_5$ are defined as in General Formula I.

In a preferred embodiment the invention provides for compounds of General Formula IV that interact with GPCRs in a biologically significant manner,

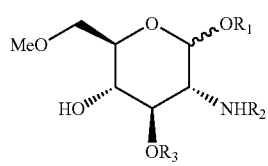

General Formula IV

Wherein $R_1$-$R_3$ are defined as in General Formula I.

In a second preferred embodiment the invention provides for compounds of General Formula V that interact with GPCRs in a biologically significant manner,

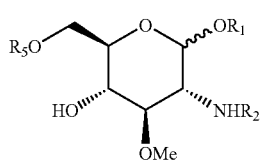

General Formula V

Where in $R_1$, $R_2$ and $R_5$ are defined as in General Formula I.

In a third preferred embodiment the invention provides for compounds of General Formula VI that interact with GPCRs in a biologically significant manner,

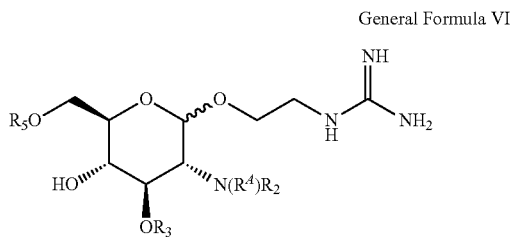

General Formula VI

Wherein $R^A$ is H or combines with $R_2$ to form an azide, and $R_3$, $R_3$ and $R_5$ are defined as in General Formula I.

In a fourth preferred embodiment the invention provides for compounds General Formula VII that interact with GPCRs in a biologically significant manner of,

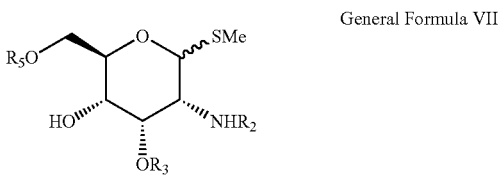

General Formula VII

Wherein, $R_2$, $R_3$ and $R_5$ are defined as in General Formula I.

In a fifth preferred embodiment the invention provides for compounds of General Formula VIII that interact with GPCRs in a biologically significant manner,

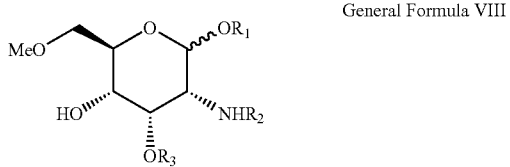

General Formula VIII

Wherein $R_1$ to $R_3$ are defined as in General Formula I.

In a sixth preferred embodiment the invention provides for compounds of General Formula IX that interact with GPCRs in a biologically significant manner,

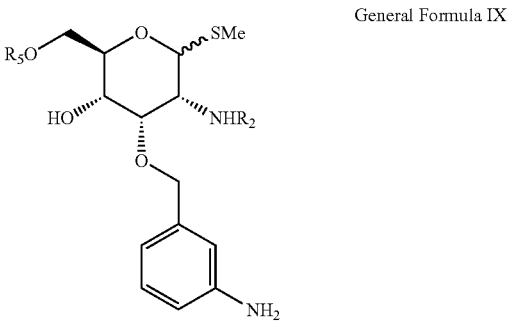

General Formula IX

Wherein $R_2$ and $R_5$ are defined as in General Formula I.

In a seventh preferred embodiment the invention provides for compounds of General Formula X that interact with GPCRs in a biologically significant manner,

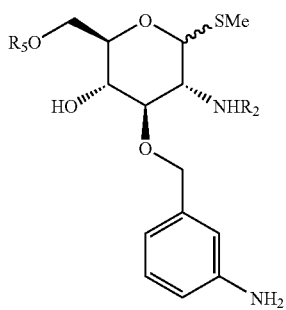

General Formula X

Wherein $R_2$ and $R_5$ are defined as in General Formula I.

In an eighth preferred embodiment the invention provides for compounds of General Formula XI that interact with GPCRs in a biologically significant manner,

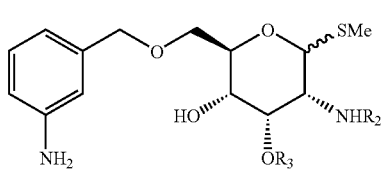

General Formula XI

Wherein $R_2$ and $R_3$ are defined as in General Formula I.

In a ninth preferred embodiment the invention provides for compounds of General Formula XII that interact with GPCRs in a biologically significant manner,

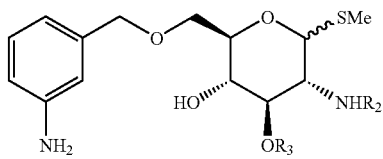

General Formula XII

Wherein $R_2$ and $R_3$ are defined as in General Formula I.

The compounds of the invention may be mixed with a pharmaceutical acceptable carrier, adjuvant, or vehicle which may comprise a-toxic carrier, adjuvant, or vehicle that may be administered to a patient, together with a compound of this invention, and which does not destroy the pharmacological activity thereof.

The pharmaceutical derivative may comprise a salt, ester, salt of an ester or other derivative of a compound of this invention which, upon administration to a recipient, is capable of providing, either directly or indirectly, a compound of this invention, although no limitation is meant thereby.

Compounds of the invention may be administered orally such as by means of a tabled, powder, liquid, emulsion, dispersion and the like; by inhalation; topically such as by means of a cream, ointment, salve etc; and as a suppository, although no limitation is meant thereby.

EXAMPLES OF THE INVENTION

Substituents per Example Libraries 1-14

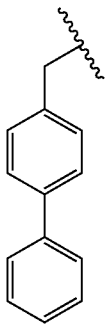

P1

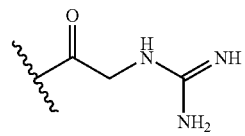

G1

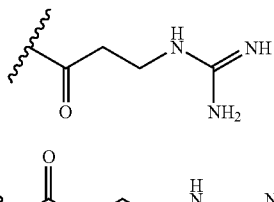

G2

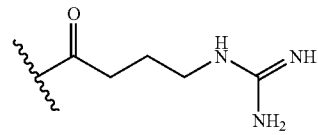

G3

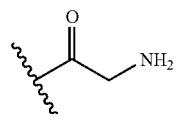

A1

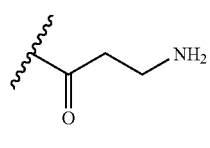

A2

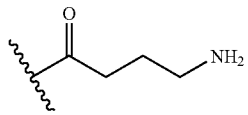

A3

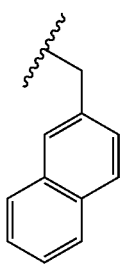

P2

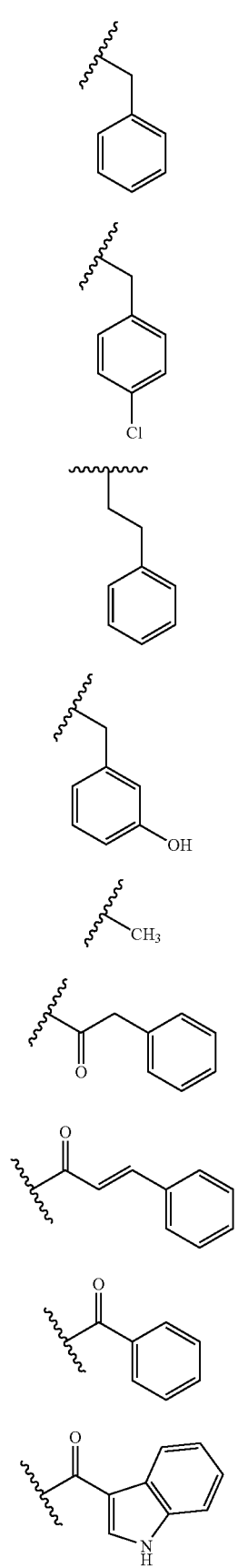
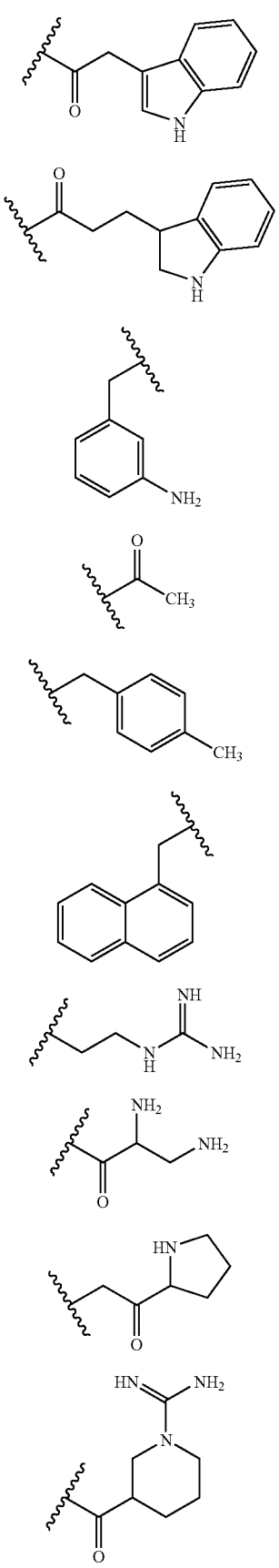

-continued

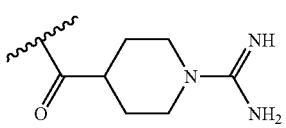

E11

Assay Conditions

GPCR Radioligand Binding (RLB) Assays

Recombinant human receptors expressed in HEK 293 cells were used for all experiments. Receptor membrane preparations were purchased from Perkin Elmer BioSignal. The labelled ligand used in somatostatin GPCR RLB assays was [$^{125}$I]SST-14 and in melanocortin assays was [$^{125}$I]NDP-αMSH. All assays were done in a 96-well plate format using either glass fiber filter mats or filter plates. All reagents purchased were of the highest quality.

Specific assay buffer, incubation and washing conditions were optimized for each receptor however they all followed the same general format. The procedures for both filter mat and filter plate formats are based on the receptor manufacturers recommendations or those described extensively in the literature. The procedures are briefly outlined below.

In assays where filter mats are used we incubate receptor membranes, assay buffer and [$^{125}$I] labelled ligand in 96 well microplates. Add compounds to incubation mixture and continue incubation for optimized period. Presoak Filter mat GF/B in 0.5% PEI for ~2 hr at 4° C. On completion of assay mixture incubation add additional 100 μL/well of assay buffer immediately prior to filtration. Filter the assay mixture onto the GF/B filter mat using a cell harvester. Dry the filter mats prior to sealing them into a scintillation counting bag with scintillant. Radioactivity in each well is detected by liquid scintillation counting.

In assays where filter plates are used Multiscreen glass fiber filter plates (Millipore, Cat No MAFCNOB10) are pre-coated with 0.5% PEI for ~2 hr at 4° C. All wells are then washed with 200 μl/well assay buffer and filtered using the Multiscreen Separation System. Subsequently receptor membranes, assay buffer and labelled ligands are added to the wells and equilibrated. Compounds for testing are then added to the mixture and incubation is continued for an optimized time. Plates are then put into the Multiscreen Separation System and the assay mixture is filtered through the plate under vacuum. Each well is then washed several times with assay buffer. Plates are then dried prior to putting sealing tape onto the bottom of the plate. Scintillant is added to each well and radioactivity measured by liquid scintillation counting.

Comparison of Assay Conditions for 2 Different Assays

|  | MC4 | SST5 |
|---|---|---|
|  | Volume μL | |
| Receptor membranes | 20 (1:40 dilution of stock) | 40 (1:40 dilution of stock) |
| labelled ligand (~80000 cpm) | 10 | 40 |
| unlabelled ligand | — | — |
| mQH$_2$O | — | — |
| Compounds | 10 | 20 |
| assay buffer | 10 | 100 |
| Total volume (μL) | 50 | 200 |

Data Analysis

Raw data was analysed according to standard methods using either GraphPad Prism software or IDDBS Activity-Base software.

Key for Assay Results Libraries 1-14

"+" Indicates inhibition greater than . . . 50%
"−" Indicates inhibition less than . . . 50%

Example Library 1

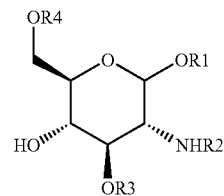

| Compound Number | R1 | R2 | R3 | R4 | MC4 inhibition at 10 micromolar | SST5 inhibition at 10 micromolar |
|---|---|---|---|---|---|---|
| 1 | P1 | G1 | P1 | P7 | + | + |
| 2 | P1 | G2 | P2 | P7 | − | + |
| 3 | P1 | A3 | P3 | P7 | − | + |
| 4 | P2 | A3 | P3 | P7 | − | + |
| 5 | P3 | G1 | P1 | P7 | + | − |
| 6 | P3 | G2 | P1 | P7 | + | + |
| 7 | P3 | A3 | P1 | P7 | − | + |
| 8 | P3 | G3 | P1 | P7 | − | + |
| 9 | P3 | A3 | P3 | P7 | − | + |
| 10 | P3 | G2 | P4 | P7 | − | + |
| 11 | P3 | A3 | P4 | P7 | − | + |
| 12 | P3 | G3 | P4 | P7 | − | + |
| 13 | P4 | G2 | P1 | P7 | + | + |
| 14 | P4 | G2 | P2 | P7 | + | + |
| 15 | P4 | G3 | P2 | P7 | + | + |
| 16 | P4 | A3 | P3 | P7 | − | + |
| 17 | P4 | G2 | P4 | P7 | − | + |
| 18 | P4 | G3 | P4 | P7 | − | + |
| 19 | P5 | G1 | P1 | P7 | + | − |
| 20 | P5 | G2 | P1 | P7 | + | − |
| 21 | P6 | G2 | P1 | P7 | − | + |
| 22 | P1 | A3 | P6 | P7 | − | + |
| 23 | P2 | A3 | P6 | P7 | − | + |
| 24 | P2 | G3 | P6 | P7 | − | + |
| 25 | P3 | A3 | P6 | P7 | − | + |
| 26 | P4 | A3 | P6 | P7 | − | + |
| 27 | P5 | A3 | P6 | P7 | − | + |
| 28 | P1 | A3 | P1 | P7 | + | + |
| 29 | P1 | G3 | P1 | P7 | + | + |
| 30 | P1 | G3 | P2 | P7 | + | + |
| 31 | P1 | G2 | P3 | P7 | − | + |
| 32 | P1 | G2 | P4 | P7 | + | + |
| 33 | P1 | A3 | P4 | P7 | + | + |
| 34 | P1 | G3 | P4 | P7 | + | + |
| 35 | P2 | G1 | P1 | P7 | + | + |
| 36 | P2 | G2 | P1 | P7 | + | + |
| 37 | P2 | A3 | P1 | P7 | + | + |
| 38 | P2 | G2 | P2 | P7 | + | + |
| 39 | P2 | A3 | P2 | P7 | + | + |
| 40 | P2 | G3 | P2 | P7 | + | + |
| 41 | P2 | G3 | P3 | P7 | − | + |
| 42 | P2 | A3 | P4 | P7 | − | + |
| 43 | P2 | G3 | P4 | P7 | + | + |
| 44 | P4 | A3 | P1 | P7 | − | + |
| 45 | P4 | G3 | P1 | P7 | + | + |
| 46 | P4 | A3 | P2 | P7 | + | + |
| 47 | P4 | G3 | P3 | P7 | − | + |
| 48 | P5 | A3 | P1 | P7 | − | + |
| 49 | P5 | G3 | P1 | P7 | + | + |
| 50 | P5 | A3 | P2 | P7 | − | + |
| 51 | P5 | A3 | P4 | P7 | + | + |
| 52 | P5 | G3 | P4 | P7 | − | + |

-continued

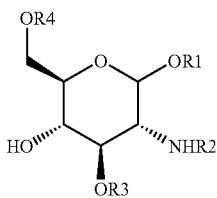

| Compound Number | R1 | R2 | R3 | R4 | MC4 inhibition at 10 micromolar | SST5 inhibition at 10 micromolar |
|---|---|---|---|---|---|---|
| 53 | P1 | A3 | P1 | P7 | + | + |
| 54 | P3 | A3 | P2 | P7 | — | + |
| 55 | P4 | A3 | P4 | P7 | — | + |

Example Library 2

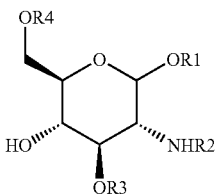

| Compound Number | R1 | R2 | R3 | R4 | MC4 Inhibition at 10 micromolar | SST5 inhibition at 10 micromolar |
|---|---|---|---|---|---|---|
| 56 | P1 | G1 | P7 | P1 | + | + |
| 57 | P1 | G2 | P7 | P1 | + | + |
| 58 | P1 | G3 | P7 | P1 | + | — |
| 59 | P1 | G1 | P7 | P2 | + | — |
| 60 | P1 | G2 | P7 | P2 | — | + |
| 61 | P1 | A3 | P7 | P2 | + | + |
| 62 | P1 | G3 | P7 | P2 | + | — |
| 63 | P1 | G1 | P7 | P4 | + | — |
| 64 | P1 | G2 | P7 | P4 | + | — |
| 65 | P1 | A3 | P7 | P4 | + | — |
| 66 | P1 | G3 | P7 | P4 | + | — |
| 67 | P2 | G1 | P7 | P1 | + | — |
| 68 | P2 | G2 | P7 | P1 | + | — |
| 69 | P2 | A3 | P7 | P1 | + | + |
| 70 | P2 | G3 | P7 | P1 | + | — |
| 71 | P2 | G1 | P7 | P2 | + | — |
| 72 | P2 | G2 | P7 | P2 | + | — |
| 73 | P2 | A3 | P7 | P2 | + | + |
| 74 | P2 | G3 | P7 | P2 | + | — |
| 75 | P2 | G1 | P7 | P4 | + | — |
| 76 | P2 | G2 | P7 | P4 | + | — |
| 77 | P2 | A3 | P7 | P4 | + | + |
| 78 | P2 | G3 | P7 | P4 | + | — |
| 79 | P3 | G3 | P7 | P1 | + | — |
| 80 | P3 | G1 | P7 | P2 | + | + |
| 81 | P3 | A3 | P7 | P4 | + | — |
| 82 | P3 | G3 | P7 | P4 | + | — |
| 83 | P4 | G1 | P7 | P1 | + | — |
| 84 | P4 | G2 | P7 | P1 | + | + |
| 85 | P4 | A3 | P7 | P1 | + | — |
| 86 | P4 | G3 | P7 | P1 | + | + |
| 87 | P4 | G1 | P7 | P2 | + | + |
| 88 | P4 | G2 | P7 | P2 | + | + |
| 89 | P4 | A3 | P7 | P2 | + | + |
| 90 | P4 | G3 | P7 | P2 | + | + |
| 91 | P4 | A3 | P7 | P3 | — | + |
| 92 | P4 | G1 | P7 | P4 | + | — |
| 93 | P4 | G2 | P7 | P4 | + | — |
| 94 | P4 | A3 | P7 | P4 | + | + |
| 95 | P4 | G3 | P7 | P4 | + | — |
| 96 | P5 | G1 | P7 | P1 | + | — |
| 97 | P5 | G2 | P7 | P1 | + | — |

-continued

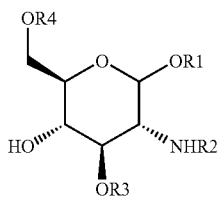

| Compound Number | R1 | R2 | R3 | R4 | MC4 Inhibition at 10 micromolar | SST5 Inhibition at 10 micromolar |
|---|---|---|---|---|---|---|
| 98 | P5 | A3 | P7 | P1 | + | + |
| 99 | P5 | G3 | P7 | P1 | + | — |
| 100 | P5 | G1 | P7 | P2 | + | — |
| 101 | P5 | G2 | P7 | P2 | + | — |
| 102 | P5 | A3 | P7 | P2 | + | + |
| 103 | P5 | G3 | P7 | P2 | + | + |
| 104 | P5 | G1 | P7 | P4 | + | — |
| 105 | P5 | G2 | P7 | P4 | + | — |
| 106 | P5 | A3 | P7 | P4 | + | + |
| 107 | P5 | G3 | P7 | P4 | + | — |
| 108 | P1 | G1 | P7 | P6 | + | — |
| 109 | P2 | A3 | P7 | P6 | — | + |
| 110 | P4 | G2 | P7 | P6 | + | — |
| 111 | P4 | A3 | P7 | P6 | — | + |
| 112 | P6 | G1 | P7 | P1 | + | — |
| 113 | P6 | G2 | P7 | P1 | + | — |
| 114 | P6 | A3 | P7 | P1 | + | — |
| 115 | P6 | G3 | P7 | P2 | + | — |
| 116 | P6 | G2 | P7 | P2 | + | — |
| 117 | P6 | G3 | P7 | P2 | + | — |
| 118 | P6 | A3 | P7 | P4 | — | + |

Example Library 3

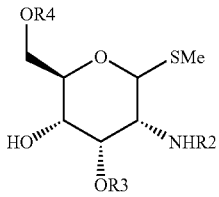

| Compound Number | R2 | R3 | R4 | MC4 inhibition at 10 micromolar | SST5 inhibition at 10 micromolar |
|---|---|---|---|---|---|
| 119 | A1 | P3 | P3 | — | + |
| 120 | G1 | P3 | P3 | + | + |
| 121 | A2 | P3 | P3 | + | + |
| 122 | G2 | P3 | P3 | + | + |
| 123 | A3 | P3 | P3 | — | + |
| 124 | G3 | P3 | P3 | + | + |
| 125 | A1 | P3 | P4 | — | + |
| 126 | G1 | P3 | P4 | + | + |
| 127 | A2 | P3 | P4 | — | + |
| 128 | G2 | P3 | P4 | + | + |
| 129 | A3 | P3 | P4 | + | + |
| 130 | G3 | P3 | P4 | + | + |
| 131 | A1 | P3 | P1 | — | + |
| 132 | G1 | P3 | P1 | + | + |
| 133 | A2 | P3 | P1 | + | + |
| 134 | G2 | P3 | P1 | + | + |
| 135 | A3 | P3 | P1 | + | + |
| 136 | G3 | P3 | P1 | + | + |
| 137 | A1 | P3 | P2 | + | + |
| 138 | G1 | P3 | P2 | + | + |
| 139 | A2 | P3 | P2 | + | + |
| 140 | G2 | P3 | P2 | + | + |
| 141 | A3 | P3 | P2 | + | + |
| 142 | G3 | P3 | P2 | + | + |

-continued

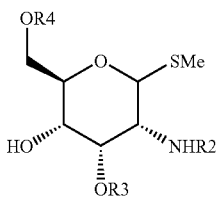

| Compound Number | R2 | R3 | R4 | MC4 inhibition at 10 micromolar | SST5 inhibition at 10 micromolar |
|---|---|---|---|---|---|
| 143 | A1 | P4 | P3 | — | + |
| 144 | G1 | P4 | P3 | + | + |
| 145 | A2 | P4 | P3 | + | + |
| 146 | G2 | P4 | P3 | + | + |
| 147 | A3 | P4 | P3 | — | + |
| 148 | G3 | P4 | P3 | + | + |
| 149 | A1 | P4 | P4 | — | + |
| 150 | G1 | P4 | P4 | + | + |
| 151 | A2 | P4 | P4 | + | + |
| 152 | G2 | P4 | P4 | + | + |
| 153 | A3 | P4 | P4 | — | + |
| 154 | G3 | P4 | P4 | + | + |
| 155 | A1 | P4 | P1 | + | + |
| 156 | G1 | P4 | P1 | + | + |
| 157 | A2 | P4 | P1 | + | + |
| 158 | G2 | P4 | P1 | + | + |
| 159 | A3 | P4 | P1 | + | + |
| 160 | G3 | P4 | P1 | + | + |
| 161 | A1 | P4 | P2 | + | + |
| 162 | G1 | P4 | P2 | + | + |
| 163 | A2 | P4 | P2 | + | + |
| 164 | G2 | P4 | P2 | + | + |
| 165 | A3 | P4 | P2 | + | + |
| 166 | G3 | P4 | P2 | + | + |
| 167 | A1 | P1 | P3 | + | + |
| 168 | G1 | P1 | P3 | + | + |
| 169 | A2 | P1 | P3 | + | + |
| 170 | G2 | P1 | P3 | + | + |
| 171 | A3 | P1 | P3 | + | + |
| 172 | G3 | P1 | P3 | + | + |
| 173 | A1 | P1 | P4 | + | + |
| 174 | G1 | P1 | P4 | + | + |
| 175 | A2 | P1 | P4 | + | + |
| 176 | G2 | P1 | P4 | + | + |
| 177 | A3 | P1 | P4 | + | + |
| 178 | G3 | P1 | P4 | + | + |
| 179 | A1 | P1 | P1 | + | + |
| 180 | G1 | P1 | P1 | + | + |
| 181 | A2 | P1 | P1 | + | + |
| 182 | G2 | P1 | P1 | + | + |
| 183 | A3 | P1 | P1 | + | + |
| 184 | G3 | P1 | P1 | — | + |
| 185 | A1 | P1 | P2 | + | — |
| 186 | G1 | P1 | P2 | + | + |
| 187 | A2 | P1 | P2 | + | + |
| 188 | G2 | P1 | P2 | + | + |
| 189 | A3 | P1 | P2 | + | + |
| 190 | G3 | P1 | P2 | + | + |
| 191 | A1 | P2 | P3 | + | + |
| 192 | G1 | P2 | P3 | + | + |
| 193 | A2 | P2 | P3 | — | + |
| 194 | G2 | P2 | P3 | + | + |
| 195 | A3 | P2 | P3 | + | + |
| 196 | G3 | P2 | P3 | + | + |
| 197 | A1 | P2 | P4 | + | + |
| 198 | G1 | P2 | P4 | + | + |
| 199 | A2 | P2 | P4 | + | + |
| 200 | G2 | P2 | P4 | + | + |
| 201 | A3 | P2 | P4 | + | + |
| 202 | G3 | P2 | P4 | + | + |
| 203 | A1 | P2 | P1 | + | + |
| 204 | G1 | P2 | P1 | + | + |
| 205 | A2 | P2 | P1 | + | + |
| 206 | G2 | P2 | P1 | + | + |
| 207 | A3 | P2 | P1 | + | + |
| 208 | G3 | P2 | P1 | + | + |
| 209 | A1 | P2 | P2 | + | + |

-continued

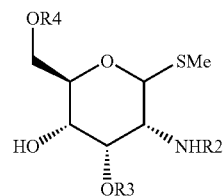

| Compound Number | R2 | R3 | R4 | MC4 inhibition at 10 micromolar | SST5 inhibition at 10 micromolar |
|---|---|---|---|---|---|
| 210 | G1 | P2 | P2 | + | + |
| 211 | A2 | P2 | P2 | + | + |
| 212 | G2 | P2 | P2 | + | + |

Example Library 4

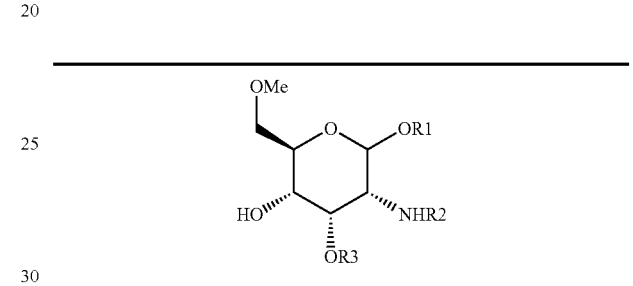

| Compound Number | R1 | R2 | R3 | MC4 inhibition at 10 micromolar | SST5 inhibition at 10 micromolar |
|---|---|---|---|---|---|
| 213 | P3 | A1 | P3 | — | + |
| 214 | P3 | G1 | P3 | + | + |
| 215 | P3 | A2 | P3 | — | + |
| 216 | P3 | G2 | P3 | + | + |
| 217 | P3 | A3 | P3 | — | + |
| 218 | P3 | G3 | P3 | + | + |
| 219 | P3 | A1 | P4 | + | + |
| 220 | P3 | G1 | P4 | + | + |
| 221 | P3 | A2 | P4 | + | + |
| 222 | P3 | G2 | P4 | + | + |
| 223 | P3 | A3 | P4 | + | + |
| 224 | P3 | G3 | P4 | + | + |
| 225 | P3 | A1 | P1 | + | + |
| 226 | P3 | G1 | P1 | + | + |
| 227 | P3 | A2 | P1 | + | + |
| 228 | P3 | G2 | P1 | + | + |
| 229 | P3 | A3 | P1 | + | + |
| 230 | P3 | G3 | P1 | + | + |
| 231 | P3 | A1 | P2 | — | + |
| 232 | P3 | G1 | P2 | + | + |
| 233 | P3 | A2 | P2 | + | + |
| 234 | P3 | G2 | P2 | + | + |
| 235 | P3 | A3 | P2 | + | + |
| 236 | P3 | G3 | P2 | + | + |
| 237 | P4 | G1 | P3 | + | + |
| 238 | P4 | A2 | P3 | — | + |
| 239 | P4 | G2 | P3 | + | + |
| 240 | P4 | A3 | P3 | — | + |
| 241 | P4 | G3 | P3 | + | + |
| 242 | P4 | A1 | P4 | + | + |
| 243 | P4 | G1 | P4 | + | + |
| 244 | P4 | A2 | P4 | + | + |
| 245 | P4 | G2 | P4 | + | + |
| 246 | P4 | A3 | P4 | + | + |
| 247 | P4 | G3 | P4 | + | + |
| 248 | P4 | A1 | P1 | + | + |
| 249 | P4 | G1 | P1 | + | + |
| 250 | P4 | A2 | P1 | + | + |
| 251 | P4 | G2 | P1 | + | + |
| 252 | P4 | A3 | P1 | + | + |
| 253 | P4 | G3 | P1 | + | + |
| 254 | P4 | A1 | P2 | + | + |

-continued

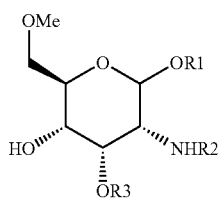

| Compound Number | R1 | R2 | R3 | MC4 inhibition at 10 micromolar | SSTS inhibition at 10 micromolar |
|---|---|---|---|---|---|
| 255 | P4 | G1 | P2 | + | + |
| 256 | P4 | A2 | P2 | + | + |
| 257 | P4 | G2 | P2 | + | + |
| 258 | P4 | A3 | P2 | + | + |
| 259 | P4 | G3 | P2 | + | + |
| 260 | P5 | A1 | P3 | — | + |
| 261 | P5 | G1 | P3 | + | |
| 262 | P5 | A2 | P3 | — | + |
| 263 | P5 | G2 | P3 | + | + |
| 264 | P5 | A3 | P3 | — | + |
| 265 | P5 | G3 | P3 | + | + |
| 266 | P5 | A1 | P4 | — | + |
| 267 | P5 | G1 | P4 | + | + |
| 268 | P5 | A2 | P4 | + | + |
| 269 | P5 | G2 | P4 | + | + |
| 270 | P5 | A3 | P4 | + | + |
| 271 | P5 | G3 | P4 | + | + |
| 272 | P5 | A1 | P1 | + | + |
| 273 | P5 | G1 | P1 | + | + |
| 274 | P5 | A1 | P1 | + | + |
| 275 | P5 | G2 | P1 | + | + |
| 276 | P5 | A3 | P1 | + | + |
| 277 | P5 | G3 | P1 | + | + |
| 278 | P5 | A1 | P2 | + | + |
| 279 | P5 | G1 | P2 | + | + |
| 280 | P5 | A1 | P2 | + | + |
| 281 | P5 | G2 | P2 | + | + |
| 282 | P5 | A3 | P2 | + | + |
| 283 | P5 | G3 | P2 | + | + |
| 284 | P2 | A1 | P3 | — | + |
| 285 | P2 | G1 | P3 | + | + |
| 286 | P2 | A1 | P3 | + | + |
| 287 | P2 | G2 | P3 | + | + |
| 288 | P2 | A3 | P3 | — | + |
| 289 | P2 | G3 | P3 | — | + |
| 290 | P2 | A1 | P4 | — | + |
| 291 | P2 | G1 | P4 | + | + |
| 292 | P2 | A2 | P4 | — | + |
| 293 | P2 | G2 | P4 | + | + |
| 294 | P2 | A3 | P4 | + | + |
| 295 | P2 | G3 | P4 | + | + |
| 296 | P2 | A1 | P1 | — | + |
| 297 | P2 | G1 | P1 | + | + |
| 298 | P2 | A1 | P1 | + | + |
| 299 | P2 | G2 | P1 | + | + |
| 300 | P2 | A3 | P1 | + | + |
| 301 | P2 | G3 | P1 | + | + |
| 302 | P2 | A1 | P2 | + | + |
| 303 | P2 | G1 | P2 | + | + |
| 304 | P2 | A2 | P2 | — | + |
| 305 | P2 | G2 | P2 | + | + |
| 306 | P2 | A3 | P2 | — | + |
| 307 | P2 | G3 | P2 | + | + |

Example Library 5

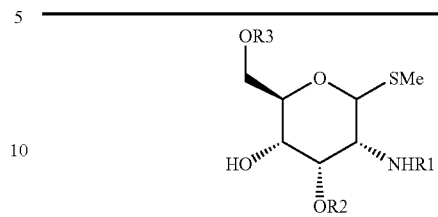

| Compound Number | R1 | A1 | R3 | MC4 inhibition at 10 micromolar | SST5 inhibition at 10 micromolar |
|---|---|---|---|---|---|
| 308 | P3 | N4 | E2 | + | — |
| 309 | P3 | N4 | E4 | + | — |
| 310 | P3 | N4 | E5 | — | + |
| 311 | P3 | N4 | E6 | + | + |
| 312 | P4 | N4 | E1 | — | + |
| 313 | P4 | N4 | E2 | + | + |
| 314 | P4 | N4 | E4 | + | — |
| 315 | P4 | N4 | E5 | — | + |

Example Library 6

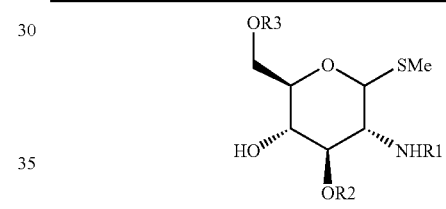

| Compound Number | R1 | R2 | R3 | MC4 inhibition at 10 micromolar | SST5 inhibition at 10 micromolar |
|---|---|---|---|---|---|
| 316 | E1 | N4 | P3 | — | + |
| 317 | E2 | N4 | P3 | + | — |
| 318 | E4 | N4 | P3 | + | + |
| 319 | E5 | N4 | P3 | — | — |
| 320 | E6 | N4 | P3 | + | + |
| 321 | E1 | N4 | P4 | — | + |
| 322 | E2 | N4 | P4 | — | + |
| 323 | E4 | N4 | P4 | + | — |
| 324 | E5 | N4 | P4 | + | + |
| 325 | E6 | N4 | P4 | + | — |

Example Library 7

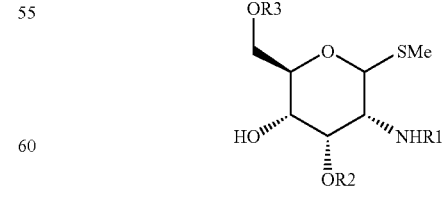

| Compound Number | R1 | R2 | R3 | MC4 inhibition at 10 micromolar | SST5 inhibition at 10 micromolar |
|---|---|---|---|---|---|
| 326 | E1 | P3 | N4 | — | + |
| 327 | E2 | P3 | N4 | + | + |

-continued

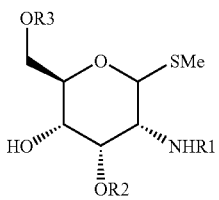

| Compound Number | R1 | R2 | R3 | MC4 inhibition at 10 micromolar | SST5 inhibition at 10 micromolar |
|---|---|---|---|---|---|
| 328 | E4 | P3 | N4 | + | — |
| 329 | E5 | P3 | N4 | — | + |
| 330 | E6 | P3 | N4 | + | + |
| 331 | E1 | P4 | N4 | + | + |
| 332 | E6 | P4 | N4 | + | — |

Example Library 8

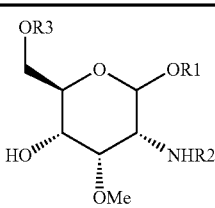

| Compound Number | R1 | R2 | R3 | MC4 inhibition at 10 micromolar | SST5 inhibition at 10 micromolar |
|---|---|---|---|---|---|
| 333 | E1 | P3 | N4 | + | — |
| 334 | E2 | P3 | N4 | + | — |
| 335 | E3 | P3 | N4 | + | — |
| 336 | E5 | P3 | N4 | + | + |
| 337 | E6 | P3 | N4 | — | + |
| 338 | E1 | P4 | N4 | + | + |
| 339 | E2 | P4 | N4 | + | + |
| 340 | E3 | P4 | N4 | + | — |
| 341 | E5 | P4 | N4 | + | + |

Example Library 9

| Compound Number | R1 | R2 | R3 | MC4 Inhibition at 4.0 Micromolar |
|---|---|---|---|---|
| 342 | P4 | E8 | P2 | + |
| 343 | P4 | E9 | P2 | + |
| 344 | P4 | E10 | P2 | + |
| 345 | P4 | G1 | P2 | + |
| 346 | P4 | E8 | P2 | + |
| 347 | P4 | E9 | P2 | + |
| 348 | P4 | E11 | P2 | + |
| 349 | P4 | G1 | P2 | + |

Example Library 10

| Compound Number | R1 | R2 | R3 | R4 | MC4 Inhibition at 4.0 Micromolar |
|---|---|---|---|---|---|
| 350 | P2 | A1 | P4 | P2 | + |
| 351 | P2 | A1 | P4 | P2 | + |
| 352 | P2 | A2 | P4 | P3 | + |
| 353 | P2 | A2 | P4 | P3 | + |
| 354 | P2 | A2 | P4 | P4 | + |
| 355 | P2 | A2 | P4 | P4 | + |
| 356 | P2 | A1 | P2 | P2 | + |
| 357 | P2 | A2 | P2 | P2 | + |
| 358 | P2 | A2 | P2 | P3 | + |
| 359 | P2 | A2 | P2 | P4 | + |
| 360 | P2 | A2 | P2 | P4 | + |
| 361 | P2 | A2 | P3 | P2 | + |
| 362 | P2 | A2 | P3 | P3 | + |
| 363 | P2 | A2 | P3 | P3 | + |
| 364 | P2 | A1 | P3 | P4 | + |
| 365 | P2 | A3 | P4 | P2 | + |
| 366 | P2 | A3 | P4 | P2 | + |
| 367 | P2 | A3 | P4 | P4 | + |
| 368 | P2 | A3 | P4 | P4 | + |
| 369 | P2 | A3 | P2 | P2 | + |
| 370 | P2 | A3 | P2 | P4 | + |
| 371 | P2 | A3 | P2 | P4 | + |
| 372 | P2 | A3 | P3 | P2 | + |
| 373 | P2 | A3 | P3 | P2 | + |
| 374 | P2 | A3 | P3 | P3 | + |
| 375 | P2 | A3 | P3 | P4 | + |
| 376 | P4 | A2 | P4 | P3 | + |
| 377 | P4 | A2 | P4 | P4 | + |
| 378 | P4 | A2 | P2 | P2 | + |
| 379 | P4 | A2 | P2 | P3 | + |
| 380 | P4 | A1 | P2 | P3 | + |
| 381 | P4 | A2 | P2 | P4 | + |
| 382 | P4 | A1 | P2 | P4 | + |
| 383 | P4 | A2 | P3 | P2 | + |
| 384 | P4 | A1 | P3 | P3 | + |
| 385 | P4 | A2 | P3 | P4 | + |
| 386 | P4 | A3 | P4 | P2 | + |
| 387 | P4 | A3 | P4 | P3 | + |
| 388 | P4 | A3 | P4 | P4 | + |
| 389 | P4 | A3 | P2 | P2 | + |
| 390 | P4 | A3 | P2 | P2 | + |
| 391 | P4 | A3 | P2 | P3 | + |
| 392 | P4 | A3 | P2 | P3 | + |
| 393 | P4 | A3 | P2 | P4 | + |
| 394 | P4 | A3 | P2 | P4 | + |
| 395 | P4 | A3 | P3 | P2 | + |
| 396 | P4 | A3 | P3 | P4 | + |

Example Library 11

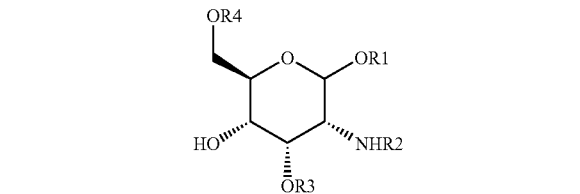

| Compound Number | R1 | R2 | R3 | R4 | MC4 Inhibition at 4.0 Micromolar |
|---|---|---|---|---|---|
| 397 | P3 | A2 | P4 | P2 | + |
| 398 | P3 | A2 | P4 | P3 | + |
| 399 | P3 | A2 | P4 | P4 | + |
| 400 | P3 | A2 | P2 | P2 | + |
| 401 | P3 | A2 | P2 | P3 | + |
| 402 | P3 | A2 | P2 | P4 | + |
| 403 | P3 | A2 | P3 | P2 | + |
| 404 | P3 | A2 | P3 | P3 | + |
| 405 | P3 | A2 | P3 | P4 | + |
| 406 | P3 | A3 | P4 | P2 | + |
| 407 | P3 | A3 | P4 | P4 | + |
| 408 | P3 | A3 | P2 | P2 | + |
| 409 | P3 | A3 | P2 | P3 | + |
| 410 | P3 | A3 | P2 | P4 | + |
| 411 | P3 | A3 | P3 | P2 | + |
| 412 | P3 | A3 | P3 | P4 | + |
| 413 | P2 | A2 | P4 | P2 | + |
| 414 | P2 | A2 | P4 | P3 | + |
| 415 | P2 | A2 | P4 | P4 | + |
| 416 | P2 | A2 | P2 | P2 | + |
| 417 | P2 | A2 | P2 | P3 | + |
| 418 | P2 | A2 | P2 | P4 | + |
| 419 | P2 | A2 | P3 | P2 | + |
| 420 | P2 | A2 | P3 | P3 | + |
| 421 | P2 | A2 | P3 | P4 | + |
| 422 | P2 | A3 | P4 | P2 | + |
| 423 | P2 | A3 | P4 | P3 | + |
| 424 | P2 | A3 | P4 | P4 | + |
| 425 | P2 | A3 | P2 | P2 | + |
| 426 | P2 | A3 | P2 | P3 | + |
| 427 | P2 | A3 | P2 | P4 | + |
| 428 | P2 | A3 | P3 | P2 | + |
| 429 | P2 | A3 | P3 | P3 | + |
| 430 | P2 | A3 | P3 | P4 | + |

Example Library 12

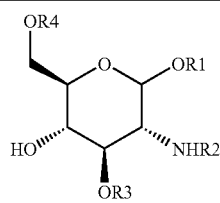

| Compound Number | R1 | R2 | R3 | R4 | MC4 Inhibition at 4.0 Micromolar |
|---|---|---|---|---|---|
| 431 | P3 | G1 | P4 | P2 | + |
| 432 | P3 | G1 | P4 | P2 | + |
| 433 | P3 | G1 | P4 | P3 | + |
| 434 | P3 | G1 | P4 | P3 | + |
| 435 | P3 | G1 | P4 | P4 | + |
| 436 | P3 | G1 | P2 | P2 | + |
| 437 | P3 | G1 | P2 | P2 | + |
| 438 | P3 | G1 | P2 | P3 | + |
| 439 | P3 | G1 | P2 | P4 | + |
| 440 | P3 | G1 | P2 | P4 | + |
| 441 | P3 | G1 | P1 | P2 | + |
| 442 | P3 | G1 | P1 | P3 | + |
| 443 | P3 | G1 | P1 | P3 | + |
| 444 | P3 | G1 | P1 | P4 | + |
| 445 | P3 | G1 | P1 | P4 | + |
| 446 | P3 | G2 | P4 | P2 | + |
| 447 | P3 | G2 | P4 | P2 | + |
| 448 | P3 | G2 | P4 | P3 | + |
| 449 | P3 | G2 | P4 | P3 | + |
| 450 | P3 | G2 | P4 | P4 | + |
| 451 | P3 | G2 | P4 | P4 | + |
| 452 | P3 | G2 | P2 | P2 | + |
| 453 | P3 | G2 | P2 | P3 | + |
| 454 | P3 | G2 | P2 | P3 | + |
| 455 | P3 | G2 | P2 | P4 | + |
| 456 | P3 | G2 | P2 | P4 | + |
| 457 | P3 | G2 | P1 | P2 | + |
| 458 | P3 | G2 | P1 | P2 | + |
| 459 | P3 | G2 | P1 | P3 | + |
| 460 | P3 | G2 | P1 | P4 | + |
| 461 | P3 | G2 | P1 | P4 | + |
| 462 | P3 | G2 | P1 | P5 | + |

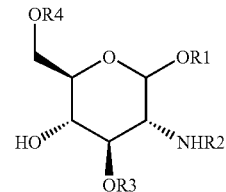

Example Library 13

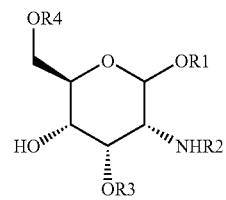

| Compound Number | R1 | R2 | R3 | R4 | MC4 Inhibition at 4.0 Micromolar |
|---|---|---|---|---|---|
| 463 | P1 | G1 | P4 | P2 | + |
| 464 | P1 | G1 | P4 | P3 | + |
| 465 | P1 | G1 | P4 | P4 | + |
| 466 | P1 | G1 | P2 | P3 | + |
| 467 | P1 | G1 | P2 | P4 | + |
| 468 | P1 | G1 | P1 | P3 | + |
| 469 | P1 | G1 | P1 | P4 | + |
| 470 | P1 | G2 | P4 | P2 | + |
| 471 | P1 | G2 | P4 | P3 | + |
| 472 | P1 | G2 | P4 | P4 | + |
| 473 | P1 | G2 | P2 | P2 | + |
| 474 | P1 | G2 | P2 | P3 | + |
| 475 | P1 | G2 | P2 | P4 | + |
| 476 | P1 | G2 | P1 | P2 | + |
| 477 | P1 | G2 | P1 | P3 | + |
| 478 | P1 | G2 | P1 | P4 | + |
| 479 | P4 | G1 | P4 | P2 | + |
| 480 | P4 | G1 | P4 | P3 | + |
| 481 | P4 | G1 | P4 | P4 | + |
| 482 | P4 | G1 | P2 | P2 | + |

-continued

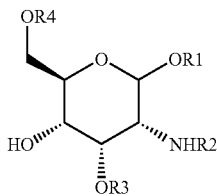

| Compound Number | R1 | R2 | R3 | R4 | MC4 Inhibition at 4.0 Micromolar |
|---|---|---|---|---|---|
| 483 | P4 | G1 | P2 | P3 | + |
| 484 | P4 | G1 | P2 | P4 | + |
| 485 | P4 | G1 | P1 | P2 | + |
| 486 | P4 | G1 | P1 | P3 | + |
| 487 | P4 | G1 | P1 | P4 | + |
| 488 | P4 | G2 | P4 | P2 | + |
| 489 | P4 | G2 | P4 | P3 | + |
| 490 | P4 | G2 | P4 | P4 | + |
| 491 | P4 | G2 | P2 | P2 | + |
| 492 | P4 | G2 | P2 | P3 | + |
| 493 | P4 | G2 | P2 | P4 | + |
| 494 | P4 | G2 | P1 | P2 | + |
| 495 | P4 | G2 | P1 | P3 | + |
| 496 | P4 | G2 | P1 | P4 | + |
| 497 | P1 | G3 | P3 | P3 | + |

Example Library 14

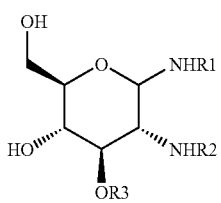

| Compound Number | R1 | R2 | R3 | MC4 Inhibition at 1.0 Micromolar |
|---|---|---|---|---|
| 498 | A2 | G4 | P3 | + |
| 499 | A2 | G4 | P12 | + |
| 500 | A2 | G4 | P13 | + |
| 501 | A2 | G4 | P1 | + |
| 502 | A2 | E1 | P3 | + |
| 503 | A2 | E1 | P4 | + |
| 504 | A2 | E1 | P12 | + |
| 505 | A2 | E1 | P13 | + |
| 506 | A1 | E1 | P3 | + |
| 507 | A1 | E1 | P4 | + |

It should be appreciated that various other changes and modifications can be made to any embodiment described without departing from the spirit and scope of the invention.

The invention claimed is:

1. A method of identifying a candidate therapeutic agent comprising:

i) contacting a membrane comprising a G-Protein Coupled Receptor (GPCR) with a compound of general formula 1, or a pharmaceutically acceptable salt thereof

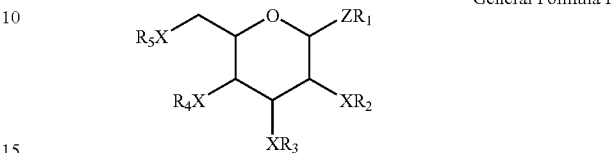

General Formula I wherein the ring may be of any configuration;

Z is selected from the group consisting of: sulphur, oxygen, and $NR^A$ wherein $R^A$ is selected from the set defined for $R_1$ to $R_5$ or C1 to C15 acyl, C4 to C15 arylacyl or C4 to C15 heteroarylacyl, with the proviso that both $R_1$ and $R^A$ are not hydrogen, X is selected from the group consisting of: oxygen and $NR^A$ providing that: i) X of $XR_2$ is $NR^A$, ii) X of $XR_3$ is oxygen and $R_3$ is not hydrogen, iii) X of $R_4$ is oxygen or $NR^A$, and X of $XR_5$ is oxygen, wherein at least one of $OR_4$ and $OR_5$ is OH, $R_1$ to $R_5$ are independently selected from the group consisting of: H, C1 to C12 alkyl, C1 to C12 alkenyl, C1 to C12 alkynyl, C1 to C12 heteroalkyl, C4 to C15 aryl, C4 to C15 heteroaryl, C4 to C15 arylalkyl and C4 to C15 heteroarylalkyl substituent, wherein, when X is $NR^A$, both $R^A$ and the corresponding $R_2$ or $R_4$ is not hydrogen, and ii) determining whether said compound inhibits or effects signal transduction activity of said GPCR, wherein a compound that inhibits or effects said activity of said GPCR is a candidate therapeutic agent.

2. The method of claim 1, wherein any one of $R^A$ or $R_1$ to $R_5$ is substituted with a moiety selected from the group consisting of: —OH, —NO, —NO$_2$, —NH$_2$, —N$_3$, —F, —Cl, —Br, —I, —CF$_3$, —CHF$_2$, —CH$_2$F, —C≡N, —OR, —C(═NH)NH$_2$, —NH—C(═NH)—NH$_2$, —COOH, —COOR, —C(═O)NHR, —NHR, —NRR, —NRRR, —NR(C═O)R, ═O, —SO$_3$H, —OSO$_2$NH$_2$, —OPO$_3$H, —OPO$_2$NH$_2$, —NH—NH$_2$, —NH—OR, —NH—OH, —SR; wherein the group R is selected from the group consisting of: H, acyl, alkyl, alkenyl, alkynyl, heteroalkyl, aryl, heteroaryl, arylalkyl, heteroarylalkyl such that the total number of carbon atoms in each of $R^A$, $R_1$, R, $R_3$, $R_4$ and $R_5$ does not exceed C1 to C15 acyl, C1 to C12 alkyl, C1 to C12 alkenyl, C1 to C12 alkynyl, C1 to C12 heteroalkyl, C4 to C15 aryl, C4 to C15 heteroaryl, C4 to C15 arylalkyl or C4 to C15 heteroarylalkyl substituent.

3. The method of claim 1, wherein the compound is

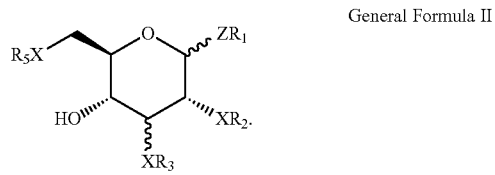

General Formula II

4. The method of claim 1, wherein the compound is

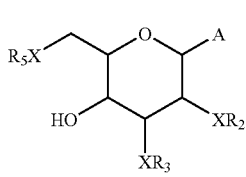
General Formula III wherein A is selected from the group consisting of: N(R⁴)R₁, SR₁, or OR₁.

5. The method of claim 1, wherein the compound is

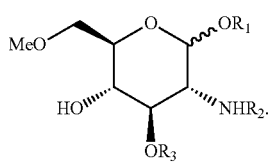
General Formula IV

6. The method of claim 1, wherein the compound is

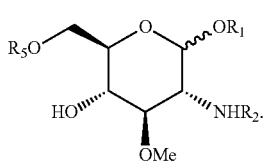
General Formula V

7. The method of claim 1, wherein the compound is

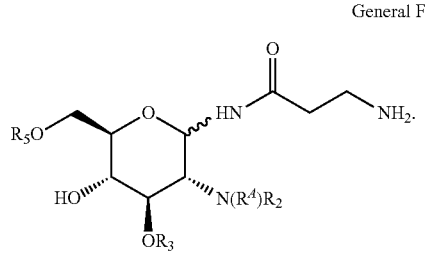
General Formula VI

8. The method of claim 1, wherein the compound is

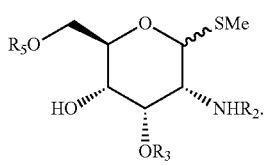
General Formula VII

9. The method of claim 1, wherein the compound is

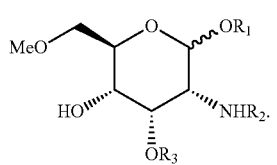
General Formula VIII

10. The method of claim 1, wherein the compound is

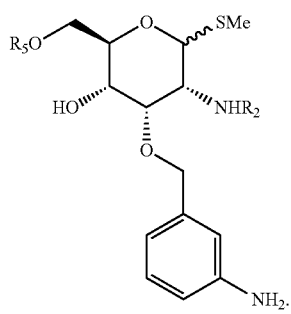
General Formula IX

11. The method of claim 1, wherein the compound is

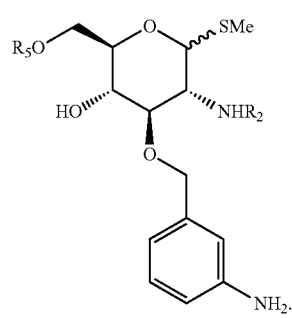
General Formula X

12. The method of claim 1, wherein the compound is

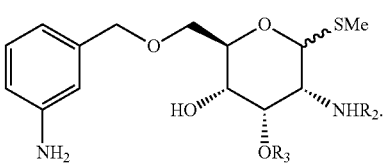
General Formula XI

13. The method of claim 1, wherein the compound is

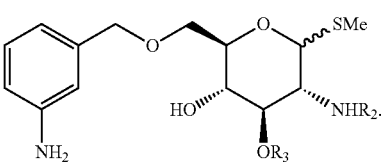
General Formula XII

14. The method of claim 1, wherein the receptor is a somatostatin receptor.

15. The method of claim 1, wherein the receptor is a melanocortin receptor.

16. The method of claim 1, wherein said membrane is in vitro.

17. The method of claim 1 wherein said membrane is ex vivo.

18. A method of identifying a candidate anti-inflammatory agent comprising:
  i) contacting a membrane comprising a G-Protein Coupled Receptor (GPCR) with a compound of general formula 1, or a pharmaceutically acceptable salt thereof

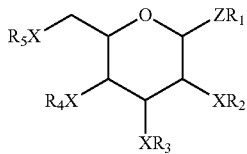

General Formula I wherein the ring may be of any configuration;
Z is selected from the group consisting of: sulphur, oxygen, and $NR^A$ wherein $R^A$ is selected from the set defined for $R_1$ to $R_5$ or C1 to C15 acyl, C4 to C15 arylacyl or C4 to C15 heteroarylacyl, with the proviso that both $R_1$ and $R^A$ are not hydrogen,
X is selected from the group consisting of: oxygen and $NR^A$ providing that: i) X of $XR_2$ is $NR^A$, ii) X of $XR_3$ is oxygen and $R_3$ is not hydrogen, iii) X of $R_4$ is oxygen or $NR^A$, and X of $XR_5$ is oxygen, wherein at least one of $OR_4$ and $OR_5$ is OH, $R_1$ to $R_5$ are independently selected from the group consisting of: H, C1 to C12 alkyl, C1 to C12 alkenyl, C1 to C12 alkynyl, C1 to C12 heteroalkyl, C4 to C15 aryl, C4 to C15 heteroaryl, C4 to C15 arylalkyl and C4 to C15 heteroarylalkyl substituent,
wherein, when X is $NR^A$, both $R^A$ and the corresponding $R_2$ or $R_4$ is not hydrogen, and
  ii) determining whether said compound inhibits or effects signal transduction activity of said GPCR,
wherein a compound that inhibits or effects said activity of said GPCR is a candidate anti-inflammatory agent.

19. A method of identifying a candidate therapeutic agent for treating pain, cancer, metabolic or gastrointestinal disorders, cardiovascular disorders, central nervous system disorders, obesity or erectile dysfunction comprising:
  i) contacting a membrane comprising a G-Protein Coupled Receptor (GPCR) with a compound of general formula 1, or a pharmaceutically acceptable salt thereof

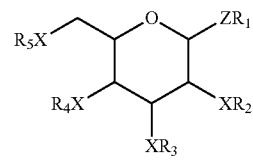

General Formula I wherein the ring may be of any configuration;
Z is selected from the group consisting of: sulphur, oxygen, and $NR^A$ wherein $R^A$ is selected from the set defined for $R_1$ to $R_5$ or C1 to C15 acyl, C4 to C15 arylacyl or C4 to C15 heteroarylacyl, with the proviso that both $R_1$ and $R^A$ are not hydrogen,
X is selected from the group consisting of: oxygen and $NR^A$ providing that: i) X of $XR_2$ is $NR^A$, ii) X of $XR_3$ is oxygen and $R_3$ is not hydrogen, iii) X of $R_4$ is oxygen or $NR^A$, and X of $XR_5$ is oxygen, wherein at least one of $OR_4$ and $OR_5$ is OH, $R_1$ to $R_5$ are independently selected from the group consisting of: H, C1 to C12 alkyl, C1 to C12 alkenyl, C1 to C12 alkynyl, C1 to C12 heteroalkyl, C4 to C15 aryl, C4 to C15 heteroaryl, C4 to C15 arylalkyl and C4 to C15 heteroarylalkyl substituent,
wherein, when X is $NR^A$, both $R^A$ and the corresponding $R_2$ or $R_4$ is not hydrogen, and
  ii) determining whether said compound inhibits or effects signal transduction activity of said GPCR,
wherein a compound that inhibits or effects said activity of said GPCR is a candidate therapeutic agent for treating pain, cancer, metabolic or gastrointestinal disorders, cardiovascular disorders, central nervous system disorders, obesity or erectile dysfunction.

* * * * *